United States Patent [19]
Bathe

[11] Patent Number: 6,109,260
[45] Date of Patent: Aug. 29, 2000

[54] NITRIC OXIDE ADMINISTRATION DEVICE WITH TIMED PULSE

[75] Inventor: Duncan P. L. Bathe, Madison, Wis.

[73] Assignee: Datex-Ohmeda, Inc., Madison, Wis.

[21] Appl. No.: 09/025,382

[22] Filed: Feb. 18, 1998

[51] Int. Cl.$^7$ .......................... A61M 15/00; A61M 16/10
[52] U.S. Cl. ................ 128/203.12; 128/204.21; 128/204.23; 128/204.26; 128/205.23; 128/205.24
[58] Field of Search .................. 128/203.12, 204.18, 128/204.21, 204.23, 204.26, 205.23, 205.24

[56] References Cited

U.S. PATENT DOCUMENTS

| | | | |
|---|---|---|---|
| 4,461,293 | 7/1984 | Chen | 128/204.23 |
| 4,462,398 | 7/1984 | Durkan et al. | |
| 4,506,666 | 3/1985 | Durkan | 128/204.23 |
| 4,519,387 | 5/1985 | Durkan et al. | 128/204.23 |
| 4,570,631 | 2/1986 | Durkan | 128/204.23 |
| 4,706,664 | 11/1987 | Snook et al. | 128/204.23 |
| 4,932,402 | 6/1990 | Snook et al. | 128/204.23 |
| 4,938,212 | 7/1990 | Snook et al. | 128/204.23 |
| 5,005,570 | 4/1991 | Perkins | 128/204.23 |
| 5,038,770 | 8/1991 | Perkins | 128/204.23 |
| 5,396,882 | 3/1995 | Zapol | 128/200.14 |
| 5,485,827 | 1/1996 | Zapol et al. | 128/200.14 |
| 5,522,381 | 6/1996 | Olsso et al. | 128/203.12 |
| 5,531,218 | 7/1996 | Krebs | 128/203.12 |
| 5,558,083 | 9/1996 | Bathe et al. | 128/203.12 |
| 5,570,683 | 11/1996 | Zapol | 128/200.14 |
| 5,651,358 | 7/1997 | Briend et al. | 128/203.12 |
| 5,713,349 | 2/1998 | Keaney | 128/204.23 |
| 5,732,693 | 3/1998 | Bathe et al. | 128/203.12 |
| 5,732,694 | 3/1998 | Bathe et al. | 128/203.12 |
| 5,823,180 | 10/1998 | Zapol | 128/200.24 |
| 5,839,433 | 11/1998 | Higenbottam | 128/204.21 |
| 5,871,009 | 2/1999 | Rydren et al. | 128/203.12 |
| 5,873,359 | 2/1999 | Zapol et al. | 128/203.12 |

FOREIGN PATENT DOCUMENTS

95/10315  4/1995  WIPO.

OTHER PUBLICATIONS

Inhaled nitric oxide in persistent pulmonary hypertension of the newborn and Low–dose inhalational nitric oxide in persistent pulmonary hypertension of the newborn —The Lancet, vol. 340; Oct. 3, 1992 pp. 818–820.

Inhaled nitric oxide, the Past, the Present, and the Future—Anesthesiology, vol. 78, No. 3, Mar. 1993, pp. 413–416.

Pulsed Delivery of Inhaled Nitric Oxide to Patients with Primary Pulmonary Hypertension—Chest, vol. 109, Jun. 1996, pp. 1545–1549.

*Primary Examiner*—John G. Weiss
*Assistant Examiner*—Joseph F. Weiss, Jr.
*Attorney, Agent, or Firm*—Andrus, Sceales, Starke & Sawall

[57] ABSTRACT

A respiratory therapy apparatus is disclosed that delivers a pulsed volume of NO containing therapeutic gas to a patient upon each inhalation of the patient. The NO delivery system includes certain functions to provide protection against the inadvertent formation of $NO_2$ through the reaction of NO and $O_2$ within the device itself. Since the formation of $NO_2$ is a time based reaction, the delivery system includes a timer that monitors the elapsed time the passes between pulses of a NO containing therapy gas to the patient. In the event that time exceeds a predetermined period, thereby raising the possibility that sufficient time has passed to potentially have toxic concentrations of $NO_2$ formed, the delivery device automatically itself delivers the pulse of NO containing gas to the patient and which clears the conduits, passageways and the like within the device to rid the device of any $NO_2$ that may have formed. As a further feature, the device also counts the number of successive times that the system activates itself and when that count exceeds a predetermined number, a fault condition is recognized and an appropriate alert is signaled to the user.

16 Claims, 2 Drawing Sheets

NITRIC OXIDE ADMINISTRATION DEVICE WITH TIMED PULSE

BACKGROUND

This invention relates to the administration of a therapeutic gas such as nitric oxide (NO) to patients for therapeutic effect. In particular, it relates to a delivery system wherein a controlled pulse of NO is provided to the patient with each inhalation by the patient and to the use of various functions utilized by that system to control and/or eliminate nitrogen dioxide ($NO_2$) from the system for safety reasons.

The function of the administration of NO has been fairly widely published and typical articles appeared in The Lancet, Vol. 340, October 1992 at pages 818–820 entitled "Inhaled Nitric Oxide in Persistent Pulmonary Hypertension of the Newborn" and "Low-dose Inhalational Nitric Oxide in Persistent Pulmonary Hypertension of the Newborn" and in Anesthesiology, Vol. 78, pgs. 413–416 (1993), entitled "Inhaled NO—the past, the present and the future".

The actual administration of NO is generally carried out by its introduction into the patient as a gas and commercially available supplies are provided in cylinders under pressure and may be at pressures of about 2000 psi and consist of a predetermined mixture of NO in a carrier gas such as nitrogen. A pressure regulator is therefore used to reduce the pressure of the supply cylinder to working levels for introduction to a patient.

The concentration administered to a patient will vary according to the patient and the need for the therapy but will generally include concentrations at or lower than 150 ppm. There is, of course, a need for that concentration to be precisely metered to the patient since an excess of NO can be harmful to the patient.

One current known method and apparatus for the administration of NO to patients is described in U.S. Pat. No. 5,558,083 where a system is provided that can be added to any ventilator and which will meter in the desired concentration of NO into the gas supplied from that ventilator.

Various other delivery devices have also been used that respond to the patient attempting to inhale to deliver a pulsed dose of NO to the patient and such pulsing devices have also been shown to have therapeutic effect on the patient, for example, as described in Higenbottam PCT patent application WO 95/10315 and the publication of Channick et al "Pulsed delivery of inhaled nitric oxide to patients with primary pulmonary hypertension", Chest/109/June 1996. In such pulsatile dosing devices, a pulse of NO is administered to the patient as the patient inhales spontaneously.

The inhalation pulsing type devices are typically shown and described in Durkan, U.S. Pat. No. 4,462,398. Another such apparatus is described in copending U.S. Patent application entitled "Constant Volume NO Pulse Delivery Device", U.S. Ser. No. 08/857,924 and owned by the same assignee as the present application.

One difficulty with such devices that provide a supplemental therapeutic gas to the patient concerns the formation of $NO_2$ from NO. $NO_2$ is a toxic compound and its presence is, therefore, undesirable in any appreciable concentration in the gas administered to the patient. Such toxic effects are present at concentrations of about 3 ppm and therefore even minute quantities of $NO_2$ cannot be tolerated.

In the pulse dose devices that administer NO as a supplemental therapeutic gas to the patient, there is likely to be no monitor to sense the presence of $NO_2$ and therefore it is important to take preventative measures in the system itself to assure that the formation of $NO_2$ does not occur, or when it does occur, to remove the $NO_2$ from the system before the NO containing therapy gas is delivered to the patient.

The formation of $NO_2$ results from the reaction of NO with $O_2$ and therefore there is ample opportunity in the administration of NO to a patient for $NO_2$ to be formed since, obviously, any such administration to a patient must be accompanied by a supply of oxygen to that patient. In addition, the reaction of NO and $O_2$ to form $NO_2$ is a time related reaction, that is, the more the NO is in association with the $O_2$, the more $NO_2$ is formed, therefore it is important to provide prevention measures wherever there is any time period where the NO and $O_2$ can be in contact with each other.

Therefore, one of the critical times that the formation of $NO_2$ can take place and rise to a potentially toxic concentration is in the administration of pulses of NO containing gas where the pulse is triggered by the breath of the patient and where too long a period of time elapses between pulses, that is, for some reason the patient has not triggered a pulse to deliver the NO containing gas to that patient. Since the reaction of NO and $O_2$ is well known and the volume of the NO device relatively easy to determine, it can be calculated for such devices the critical amount of time that can elapse between pulses of NO containing therapeutic gas before the potential of toxic levels of $NO_2$ can occur. Accordingly by knowing that time, it is prudent to take preventative measures to insure that the residence time of the NO and $O_2$ containing components do not remain in any of the passageways of the NO pulse administering device for that period of time.

SUMMARY OF THE INVENTION

In accordance with the present invention, there is provided a nitric oxide delivery system where a volume of NO is administered to the patient and where certain safety steps are carried out to eliminate $NO_2$ from the system to prevent the inadvertent administration of a toxic concentration of $NO_2$ to the patient.

Therefore, as an aspect of the present invention, a timer is included that times the duration between pulses, that is, when a pulse of NO containing gas is administered to a patient, it is assumed that the patient will trigger the device to provide a subsequent pulse of NO containing gas within a reasonable period of time. That subsequent pulse will, of course also then purge the system since it will provide a fresh pulse and rid the passageways of any NO and O2 containing gas that may be reacting to form $NO_2$ in that passageway.

In accordance with the present invention, therefore, the timer will start after each pulse and will reset upon the administration of a subsequent pulse providing that subsequent pulse is triggered within the timed period. In the preferred embodiment, the timer may be set at 15 seconds, and the timer will note the elapsing of 15 seconds from the administration of any pulse. If the timer reaches the end of the 15 second period, thereby indicating that no pulse of NO containing gas has been administered during that period, the timer will itself trigger a pulse so that the device purges itself and rids the possible formation of any $NO_2$ that may have formed by the reaction of NO and O2 in the intervening time period. Thus, there cannot be a long period of time where no pulse is administered by the system and therefore no long period of time sufficient to allow a formation of $NO_2$ in a toxic level.

As a further aspect of the invention, a counter is included that counts the number of successive times the automatic activation of the pulse to the patient occurs, that is, the number of times a pulse of NO containing gas is administered to the patient without an activation of the patient triggering device. The number of such successive pulses is an indication that the patient is simply not attempting to inhale, or if attempting to inhale, the system is not properly recognizing that attempt. Accordingly, after a predetermined number of non-patient initiated pulses, the system activates an alarm to alert the user to the situation to take prompt action to determine the problem.

DETAILED DESCRIPTION OF THE INVENTION

Figure 1:
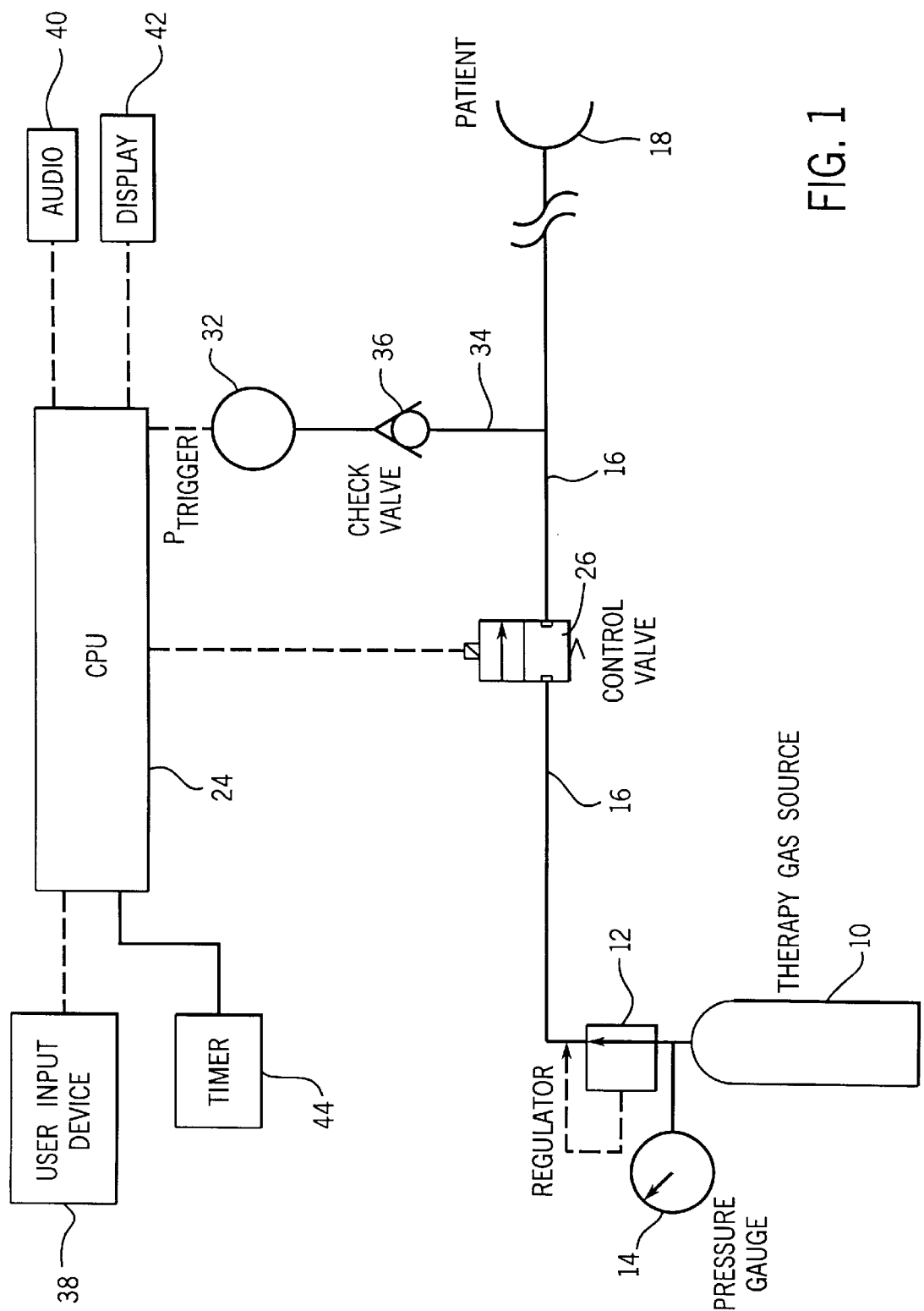
FIG. 1 is a schematic view of a NO delivery system constructed in accordance with the present invention.

Turning now to the FIG. 1, there is shown a schematic view of a pulsed dosing NO delivery apparatus constructed in accordance with the present invention. A gas cylinder 10 is provided containing the therapeutic amount of nitric oxide. Preferable that NO gas is mixed with a balance or carrier gas such as nitrogen and the concentration may be in the order of 100 ppm. The NO in nitrogen gas is available commercially in cylinders at pressures of approximately 2000 psig.

A pressure regulator 12 reduces the cylinder pressure down to a working pressure for use with the present system and that pressure may be in the order of about 50 psig. A pressure gauge 14 is generally provided on the pressure regulator 12 in order to keep track of the pressure within the gas cylinder 10.

A conduit 16 carries the NO containing therapy gas from the regulator 12 through to a patient 18 where the NO containing therapy gas is administered to the patient by means such as a nasal cannula (not shown).

A control valve 26 controls the flow of NO containing therapy gas from the gas cylinder 10 to the patient 18 and is a solenoid controlled valve operated by signal from the CPU 24. Again, for safety, the control valve 26 is normally closed and is moved to its open position when a signal energizes the valve by CPU 24. As will be explained, the time during which the control valve 26 is in the open position controls the volume of NO containing therapy gas to the patient 18.

A patient trigger 32 is in communication with the patient by means of a passageway 34 and including a check valve 36. The patient trigger 32 may be of conventional design and basically detects a negative pressure $P_{trigger}$ from the patient indicating that the patient 18 is initiating inhalation. That patient trigger 32 thus provides a signal to the CPU 24 to alert the CPU 24 that the patient is initiating an inhalation so that the CPU can take the appropriate action to open control valve 26 to provide a pulse of NO containing therapeutic gas to the patient 18 during that inhalation.

A user input device 38 allows the user to input to the CPU 24 the specific volume of NO containing therapeutic gas that is desired to be delivered to the patient 18 during each inhalation and such device may be a rotary switch or the like. Alternatively, the volume to be delivered may be predetermined by the manufacturer of the delivery system and already established in the system and not be individually selected in the field by a user. Also as a part of the system, there may be an audio alarm 40 and a visual display 42 that may also contain visual alarms as well as display various monitored conditions of the device to the user.

The overall operation of the NO dosing device may now be explained. As noted, upon start-up of the system, the gas cylinder 10 containing the NO therapy gas in a predetermined concentration is opened and the NO containing therapy gas enters the regulator 12 and the conduit 16.

The user may input a volume of NO containing therapy gas that is desired to be administered to the patient 18 by means of the user input device 38, or, as indicated, the volume of NO containing gas may be preset by the manufacturer. As the patient initiates an inhalation, the patient trigger 32 senses the negative pressure and signals the CPU 24 to commence the injection of a dosage of NO containing therapy gas to the patient 18. Initially, the CPU 24 thus opens the control valve 26 for a predetermined time or for a calculated period of time to allow the administration of the NO containing therapy gas to the patient 18 and then will move the control valve 26 to its closed position when the proper dosage of NO containing therapy gas has been delivered to the patient 18.

As may be seen, the CPU 24 includes a timer 44 and the timer 44 is shown as a separate function block, however it may be incorporated into the CPU 24 as a part of the function of the CPU 24. As will be noted, the timer 44 insures that the conduit 16 as well as any other conduits that may contain a combination of NO and $O_2$ are purged of the gases at predetermined intervals. During the normal operation of the system, the patient may inhale at various intervals and, at each inhalation, the flow therapeutic gas from the gas cylinder 10 is, of course, provided to the patient 18.

Thus, as the patient inhales, the conduits that carry the NO containing gas are continually purged with the new gas and the continual and normal inhalation and corresponding application of a therapeutic dose of NO containing gas prevents the build up of any $NO_2$ in the conduit 16.

In the present NO delivery system, therefore, as long as the system is properly functioning and the patient is being delivered a fresh dosage of NO containing therapy gas, the system does not allow a sufficient time for any particular dosage to remain in the conduit 16 and react to form a hazardous concentration of $NO_2$. In the event, however, that there is a problem with the system and for some reason, the supply of a dosage is not provided to the patient within a predetermined time, it is possible for the concentration of $NO_2$ in the conduit 16 to reach an unacceptable level.

To prevent that problem, the timer 44 commences a timing function upon the administration of any pulse dosage of NO containing therapy gas to the patient 18. As such, the timer notes the application of a pulse and then starts to determine the elapsed time until the next pulse is administered to the patient 18. As long as the subsequent pulse is administered within a predetermined safe time, the NO delivery system will continue to operate normally and after each pulse, the timer 44 will reset and determine the elapsed time until the subsequent pulse of NO containing gas.

In the event the timer 44 reaches the predetermined time, and that will only occur if no pulse of NO containing gas has been administered during that elapsed time, the timer 44 will immediately signal the CPU 24 to provide a pulse of NO containing gas as if the patient trigger 32 had been activated by the patient 18. Thus, if the patient 18 has not activated the patient trigger 32 to provide a pulse of NO containing therapy gas within a predetermined period of time, the system itself will operate to deliver that pulse, thus assuring that the conduits, and particularly within the conduit 16, is purged every predetermined time period to prevent the potential build up of a high concentration of $NO_2$.

Figure 2:
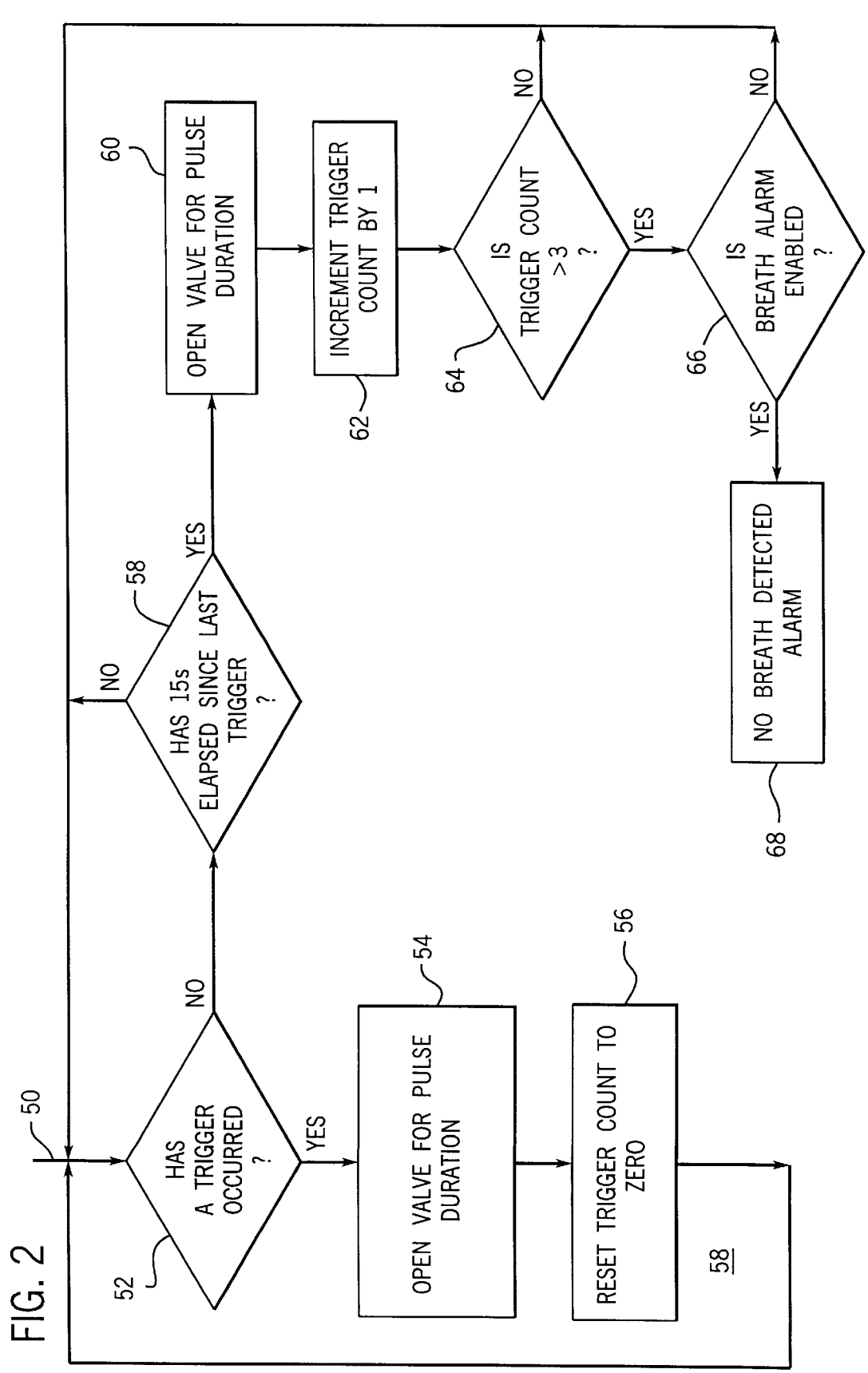
FIG. 2 is a flow chart of the system of the present invention that provides a pulse of NO containing gas after a predetermined time period.

Turning now to FIG. 2, there is shown a flow chart, taken along with FIG. 1, and which describes the overall operation of the NO delivery system. As noted, when the NO delivery system is initiated, the system administers a pulse of NO containing therapeutic gas to the patient 18 upon the patient attempting to inhale and thus activating the patient trigger 32. In FIG. 2, the overall flow of the CPU 24 functions is commenced at point 50 where CPU 24 determines if activation of the patient trigger 32 has occurred and represented by block 52. Thus, if the patient trigger 32 has been activated, the system continues in its normal operation to block 54 where the CPU 24 opens control valve 26 to deliver that pulse and the trigger count is automatically reset to zero in block 56 as will be explained.

Accordingly as long as the patient is attempting to inhale and is activating the patient trigger 32 at regular predetermined intervals, the overall system will follow the loop 58 in its normal operation.

Returning to block, 52, the timer 44 is activated upon the activation of the patient trigger 32 and delivery of the dosage of NO continuing therapy gas. At block 52 the timer function, represented by block 58, will commence to measure the elapsed time from any particular pulse delivery to the subsequent pulse initiated by the patient trigger 32. As soon as a subsequent activation of patient trigger 32 occurs, the system will allow the normal functioning and operation of the system according to the loop 58. In the event, however, that a predetermined time elapses between any activation of the patient trigger 32 and no subsequent activation has occurred, the system will proceed to block 60 and the CPU 24 will automatically open the control valve 26 to provide a dosage of NO containing gas to the patient even though the patient trigger 32 has not been activated. The automatic dosage thus provided by the system insures that no $NO_2$ can be built up in the various conduits, such as conduit 18, between the administration of successive dosages of NO containing therapy gas to the patient.

As a further feature of the present automatic pulsing system, when the opening of the control valve 26 is caused by the automatic function of block 60, the trigger count is incremented by 1 in block 62 and, in block 64, the number of times that the automatic implemented is counted and, when the trigger count reaches a predetermined number, i.e. 4, the CPU 24 will determine that something is wrong in that the patient 18 has not activated the patient trigger 32 for the last three pulse deliveries and an alarm system will be activated to see if the patients breathing is being detected. Accordingly, in block 66, the system will see if the breath alarm is enabled and if so, the audio alarm 40 or visual display 42 will be activated to alert the clinician that no breaths are being detected by the patient trigger 32 so that the clinician can take prompt corrective action.

Numerous further variations and combinations of the features discussed above can be utilized without departing from the spirit of the invention as defined by the claims below. Accordingly, the foregoing description of the preferred embodiment should be taken by way of illustration rather than by way of limitation of the invention as claimed.

What is claimed is:

1. A Nitric Oxide delivery system for delivering a therapeutic amount of nitric oxide to a patient, said system comprising:

a conduit adapted to be connected to a source therapy gas containing nitric oxide (NO) under pressure and communicating the NO containing therapy gas to a patient through a patient utilization device, a control valve in said conduit adapted to open and close to deliver the NO containing therapy gas to a patient in predetermined, timed pulses, a patient trigger device adapted to detect the inhalation of a patient and to provide a signal indicative of a patient attempting to inhale, a central processing unit receiving the signal from said patient trigger device, said central processing unit adapted to send a signal to said control valve in response to said signal from said patient trigger device to open said control valve for a predetermined time to provide a pulse of NO containing therapy gas to a patient, a timer adapted to detect a predetermined elapsed time following the delivery of a pulse of NO containing therapy gas, in which time the administration of a subsequent pulse of NO containing therapeutic gas does not occur, and to provide a signal to said central processing unit when said predetermined elapsed time has passed, and said central processing unit receiving the signal from said timer and adapted to send a signal to said control valve in response to said signal from said timer to open said control valve for a predetermined time to provide a pulse of NO containing therapy gas to flush said conduit.

2. A nitric oxide delivery system as defined in claim 1 wherein said timer its reset whenever said patient trigger device is activated to open said control valve.

3. A nitric oxide delivery system as defined in claim 1 wherein said system further includes a counter that counts the number of successive times said central processing unit opens said control valve in response to said signal from said timer to provide a pulse of NO containing therapeutic gas to a patient.

4. A nitric oxide delivery system as defined in claim 3 wherein said counter provides an indication to a user when said counter has counted a predetermined number of successive times.

5. A Nitric Oxide delivery system for delivering a therapeutic amount of nitric oxide to a patient, said system comprising:

a conduit adapted to be connected to a source therapy gas containing nitric oxide (NO) under pressure and communicating the NO containing therapy gas to a patient through a patient utilization device, a signal operated control valve in said conduit adapted to open and close to deliver the NO containing therapy gas to a patient in predetermined, timed pulses, a patient trigger device adapted to detect the inhalation of a patient and to provide a signal indicative of a patient attempting to inhale, a central processing unit receiving the signal from said patient trigger device, said central processing unit adapted to send a signal to said signal operated valve in response to said signal from said patient trigger device to open said valve for a predetermined time to provide a pulse of NO containing therapy gas to a patient, said central processing device including a timer adapted to detect a predetermined elapsed time following the delivery of a pulse of NO containing therapy gas to a patient and in which time the administration of a subsequent pulse of NO containing therapeutic gas does not occur and to provide a signal to said central processing unit when said predetermined elapsed time has passed, and said central processing unit receiving the signal from said timer and adapted to send a signal to said signal operated valve in response to said signal from said timer to open said valve for a predetermined time to provide a pulse of NO containing therapy gas to a patient to flush said conduit.

6. A nitric oxide delivery system as defined in claim 5 wherein said signal operated valve is a solenoid operated valve.

7. A nitric oxide delivery system as defined in claim 5 wherein said predetermined elapsed time is about 15 seconds.

8. A nitric oxide delivery system as defined in claim 5 wherein said central processing unit includes a counter that counts the number of successive times said central processing unit provides said signal to open said signal operated valve in response to said signal from said timer.

9. A nitric oxide delivery system as defined in claim 8 wherein said counter provides an alert to the user when said counter has counted a predetermined number of said successive times.

10. A nitric oxide delivery system as defined in claim 8 wherein said number of successive times is about 3 to 4.

11. A method of providing an automatic pulse of a NO containing therapy gas to a patient in a NO delivery system having a conduit to deliver a gas containing a nitric oxide from a source of nitric oxide to a patient, said method comprising:

(a) providing a control valve intermediate the source of nitric oxide and the patient;

(b) opening the valve to deliver a pulse of nitric oxide containing therapy gas to a patient for a predetermined dosage of the therapeutic gas, (c) sensing the inhalation of a patient to control the opening of the control valve, (d) timing elapsed times between successive sensed inhalations of a patient;

(e) determining that an elapsed time of step (d) exceeds a predetermined period of time; and (f) opening the control valve to deliver a pulse of nitric oxide containing therapy gas to flush the conduit upon determination of step (e).

12. A method of providing an automatic pulse of a NO containing therapy gas to a patient as defined in claim 11 wherein said timing step (d) further includes resetting the time upon each opening of the valve.

13. A method of providing an automatic pulse of a NO containing therapy gas to a patient as defined in claim 11 wherein step (e) is further defined as determining that an elapsed time of step (d) exceeds a predetermined period of time of about 15 seconds.

14. A method of providing an automatic pulse of a NO containing therapy gas to a patient as defined in claim 11 wherein said method further includes the step of:

(g) counting the number of successive times the control valve is opened by step (f).

15. A method of providing an automatic pulse of a NO containing therapy gas to a patient as defined in claim 14 further including the step of:

(h) alerting a user upon the counting of a predetermined number of successive times in step (g).

16. A method of providing an automatic pulse of a NO containing therapy gas to a patient as defined in claim 15 wherein step (h) is further defined as alerting a user upon the counting of a predetermined number of successive times of about 3 to 4.

* * * * *